(12) United States Patent
Van Dam et al.

(10) Patent No.: US 9,649,632 B2
(45) Date of Patent: *May 16, 2017

(54) DISPOSABLE WORLD-TO-CHIP INTERFACE FOR DIGITAL MICROFLUIDICS

(71) Applicant: THE REGENTS OF THE UNIVERSITY OF CALIFORNIA, Oakland, CA (US)

(72) Inventors: R. Michael Van Dam, Los Angeles, CA (US); Gaurav Shah, Los Angeles, CA (US); Pei-Yuin Keng, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/406,195

(22) PCT Filed: Jun. 10, 2013

(86) PCT No.: PCT/US2013/045030
§ 371 (c)(1),
(2) Date: Dec. 5, 2014

(87) PCT Pub. No.: WO2013/185142
PCT Pub. Date: Dec. 12, 2013

(65) Prior Publication Data
US 2015/0148549 A1 May 28, 2015

Related U.S. Application Data

(60) Provisional application No. 61/657,570, filed on Jun. 8, 2012.

(51) Int. Cl.
*B01L 3/00* (2006.01)
*G01N 35/10* (2006.01)
*G01N 35/00* (2006.01)

(52) U.S. Cl.
CPC ... *B01L 3/502753* (2013.01); *B01L 3/502715* (2013.01); *G01N 35/10* (2013.01);
(Continued)

(58) Field of Classification Search
CPC .......... B01J 19/0093; B01J 2219/00783; B01J 2219/00853; B01L 3/502784; B01L 2400/0427
(Continued)

(56) References Cited

U.S. PATENT DOCUMENTS 7,452,507 B2   11/2008   Renzi et al.
8,173,073 B2   5/2012    Elizarov et al.
(Continued)

FOREIGN PATENT DOCUMENTS

WO   WO 2008/091694 A2   7/2008

OTHER PUBLICATIONS

Yi, Ui-Chong et al., Soft Printing of Droplets Pre-Metered by Electrowetting, Sensors and Actuators A, 2004, 114 (2-3), 347-354.
(Continued)

*Primary Examiner* — Jill Warden
*Assistant Examiner* — Dwayne K Handy
(74) *Attorney, Agent, or Firm* — Vista IP Law Group LLP

(57) ABSTRACT

The present disclosure sets forth incorporating microfluidic chips interfaces for use with digital microfluidic processes. Methods and devices according to the present disclosure utilize compact, integrated platforms that interface with a chip upstream and downstream of the reaction, as well as between intermediate reaction steps if needed. In some embodiments these interfaces are automated, including automation of a multiple reagent process. Various reagent delivery systems and methods are also disclosed.

16 Claims, 18 Drawing Sheets

(52) U.S. Cl.
CPC . *B01L 2200/027* (2013.01); *B01L 2200/0673* (2013.01); *B01L 2300/0681* (2013.01); *B01L 2400/0487* (2013.01); *B01L 2400/0622* (2013.01); *G01N 2035/00158* (2013.01); *G01N 2035/1034* (2013.01)

(58) Field of Classification Search
USPC .......... 422/501, 502, 503, 504; 436/53, 180; 435/4, 5, 6.1
See application file for complete search history.

(56) References Cited

U.S. PATENT DOCUMENTS

| 9,005,544 | B2* | 4/2015 | Van Dam | B01J 19/0093 422/502 |
|---|---|---|---|---|
| 2009/0036668 | A1* | 2/2009 | Elizarov | B01J 19/0093 536/122 |
| 2011/0008223 | A1 | 1/2011 | Tsao et al. | |
| 2012/0264646 | A1* | 10/2012 | Link | B01F 3/0807 506/11 |

OTHER PUBLICATIONS

Colon, Luis et al., Very high pressure HPLC with 1 mm id columns, Analyst, 2004, 129, pp. 503-504.
Reichmuth, David S. et al., Microchip HPLC of Peptides and Proteins, Anal. Chem. 2005, 77, 2997-3000.
Shih, Steve C.C. et al., Dried Blood Spot Analysis by Digital Microfluidics Coupled to Nanoelectrospray Ionization Mass Spectrometry, Anal. Chem. 2012, 84, 3731-3738.
Shah, G. J. et al., Integrated digital microchemistry platform: Automation of multi-reagent loading, on-chip high-temperature reactions, and product extraction, Intl. Symposium on Microchemistry and Microsystems, Zhubei, Taiwan, Jun. 2012.
Elizarov, Arkadij et al., Design and Optimization of Coin-Shaped Microreator Chips for PET Radiopharmaceutical Synthesis, J. Nucl Med 51(2): 282 (2010).
PCT International Search Report for PCT/US2013/04030, Applicant: The Regents of the University of California, Form PCT/ISA/210 and 220, dated Sep. 11, 2013 (6 pages).
PCT Written Opinion of the International Search Authority for PCT/US2013/045030, Applicant: The Regents of the University of California Form PCT/ISA/237, dated Sep. 11, 2013 (5 pages).
Zhao et al., Digital Microfluidic Chips for Automated Hydrogen Deuterium Exchange (HDX) MS Analysis, 15th Int'l Conference on Miniaturized Systems for Chemistry and Life Sciences, Oct. 2-6, 2011, Seattle, WA, USA, pp. 1287-1289.
PCT International Preliminary Report on Patentability (Chapter I of the Patent Cooperation Treaty) for PCT/US2013/045030, Applicant: The Regents of the University of California, Form PCT/IB/326 and 373, dated Dec. 18, 2014 (7pages).
Shah, G.J. et al., Milliliter-to-Microliter Platform for On-Demand Loading of Aqueous and Non-Aqueous Droplets to Digital Microfluidics, Transducers' 11, Beijing, China, Jun. 5-9, 2011, 1260-1263.

* cited by examiner

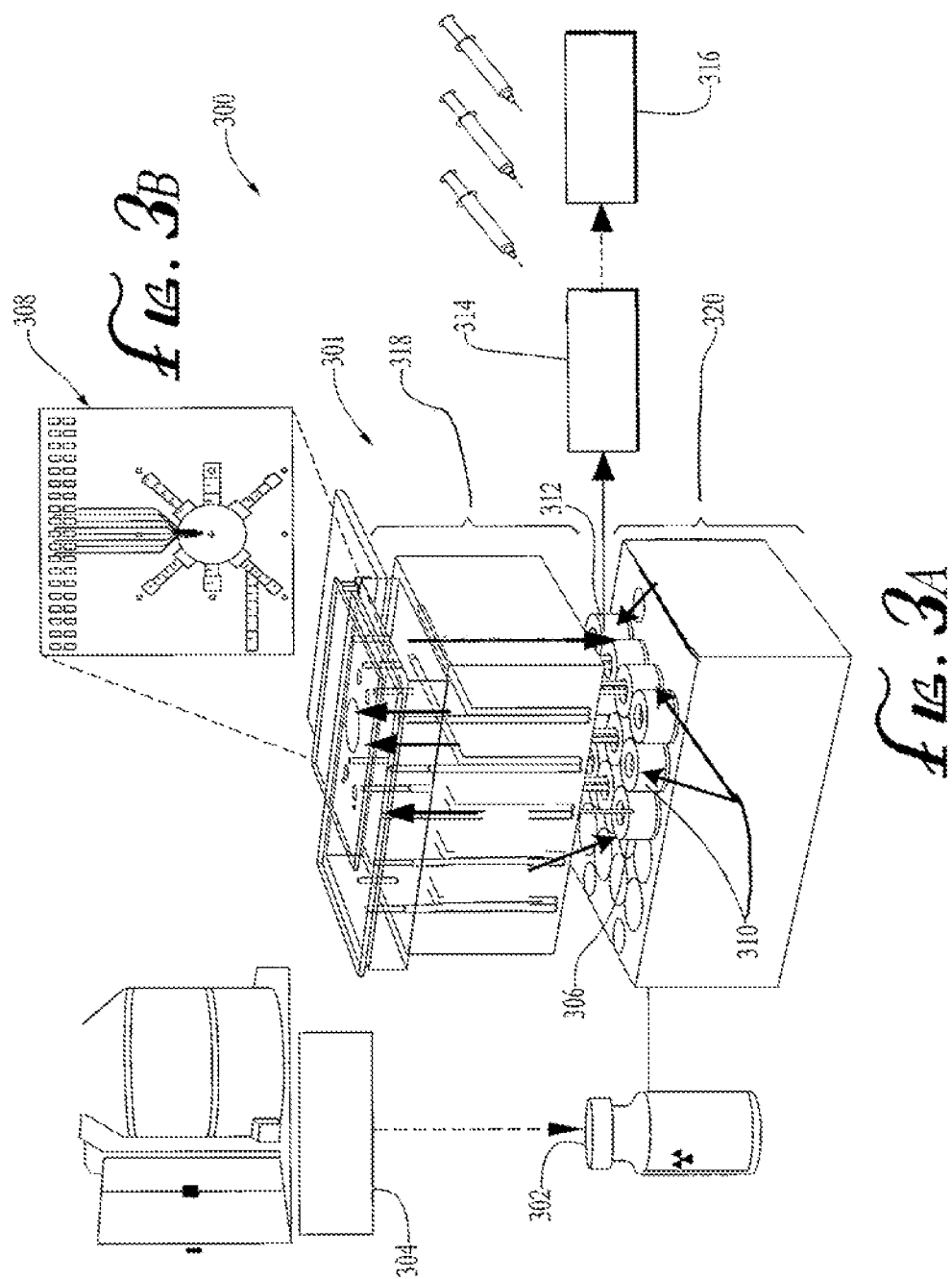

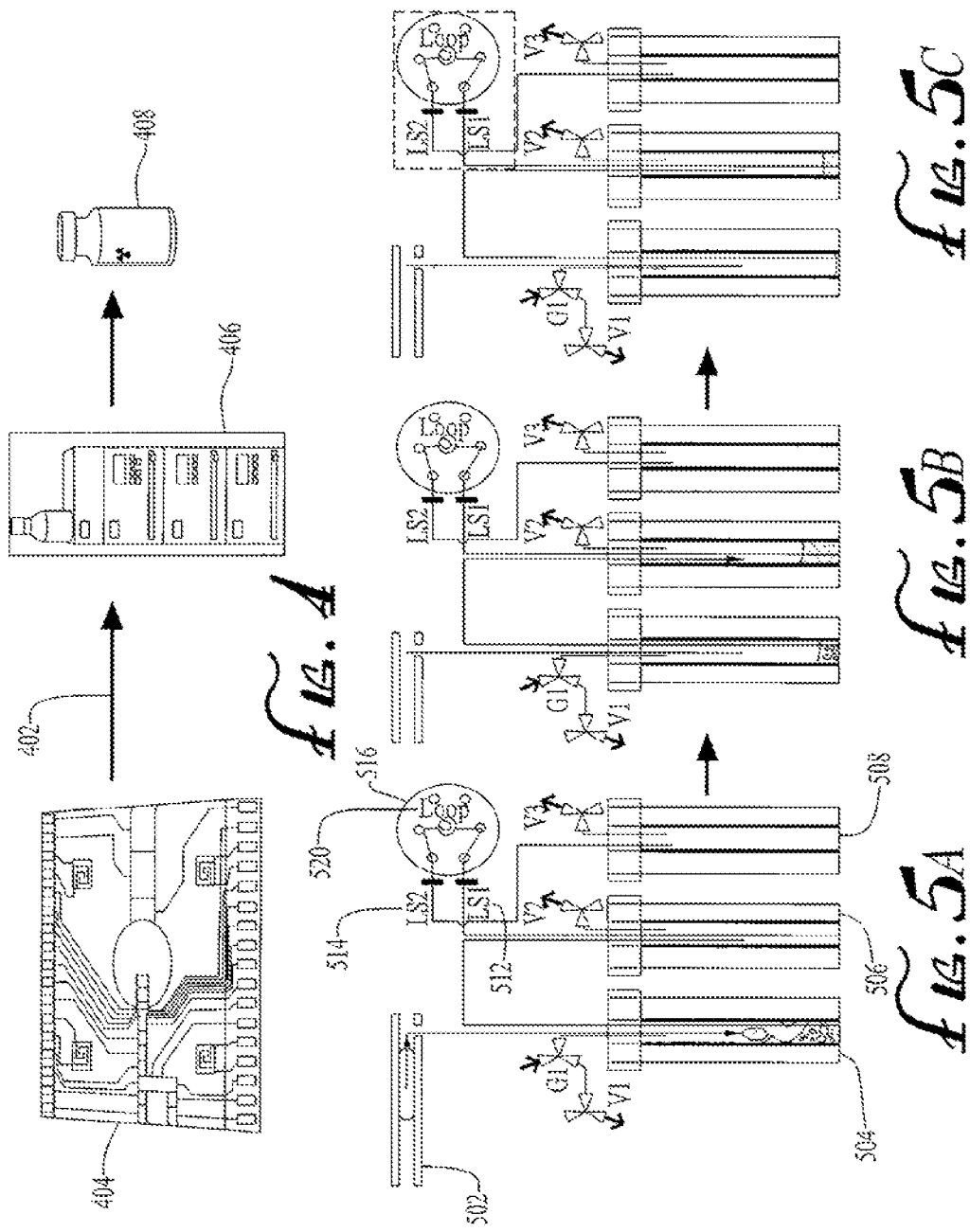

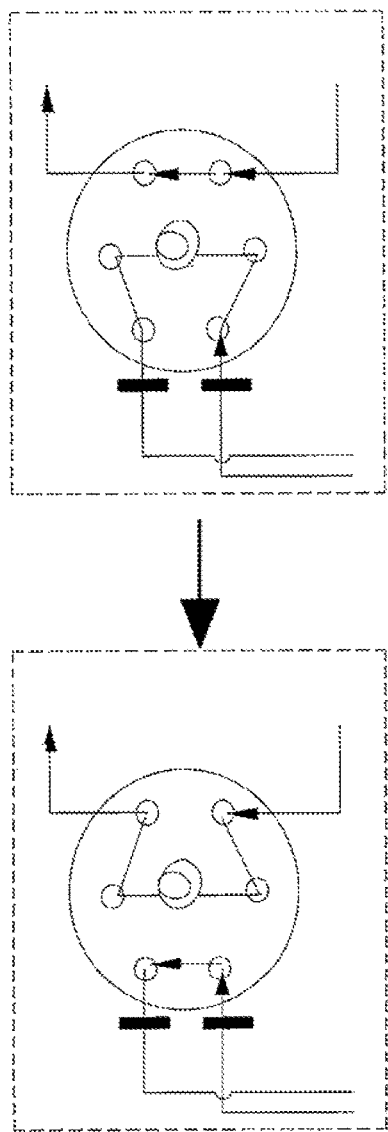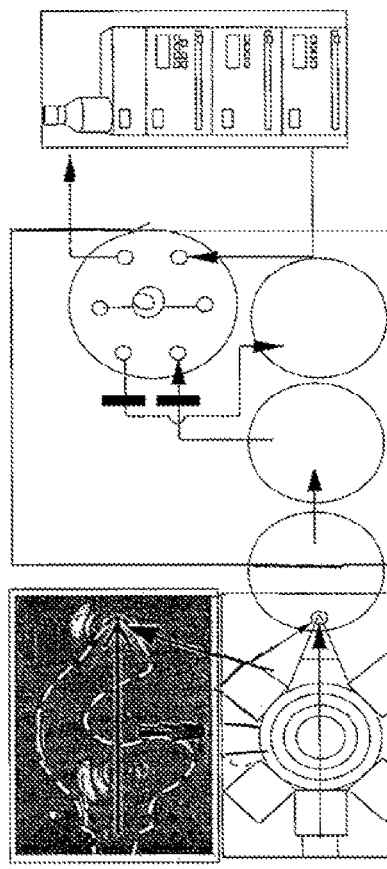
Fig. 5D
Fig. 5E
Fig. 5F

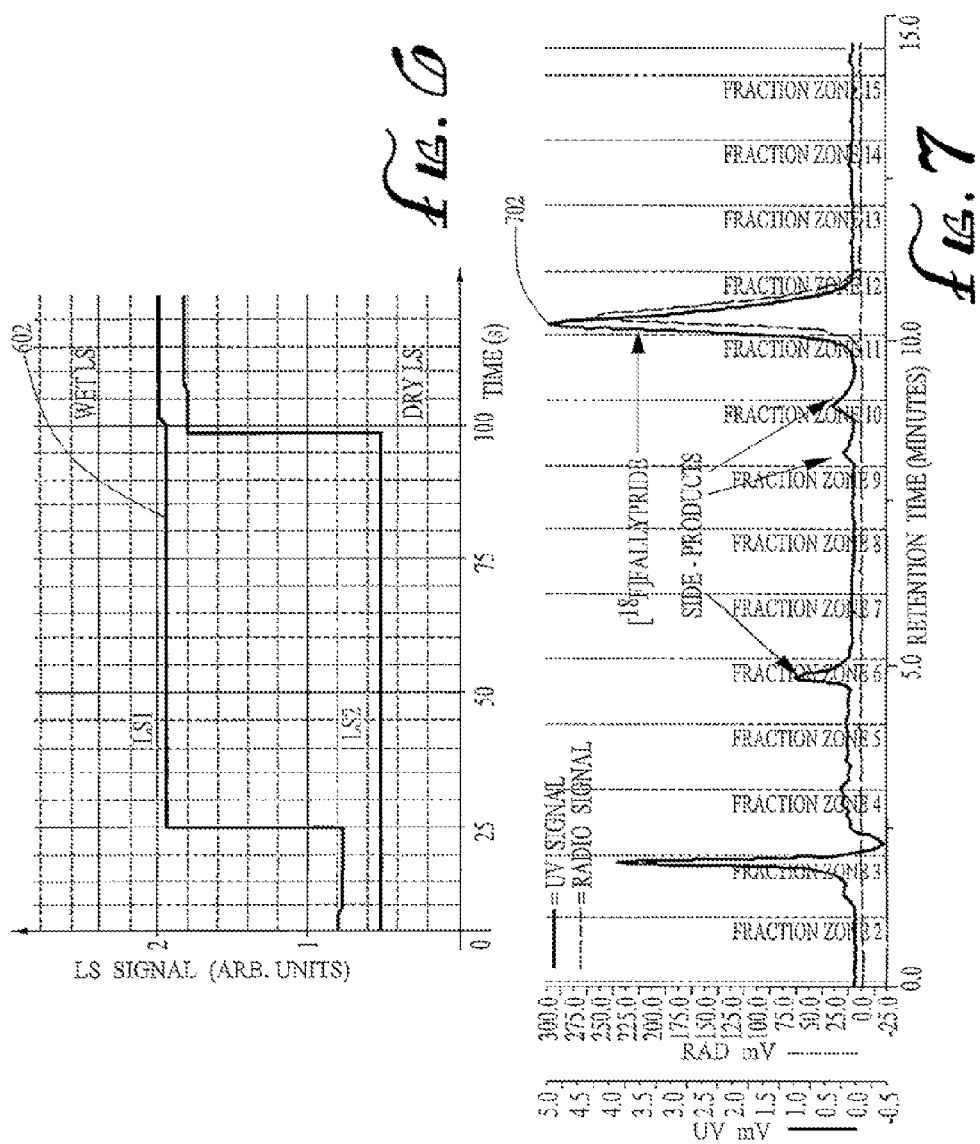

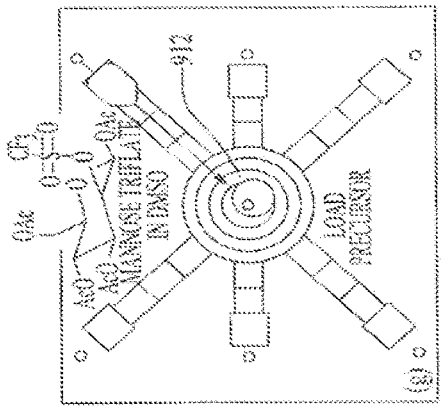
Fig. 9A
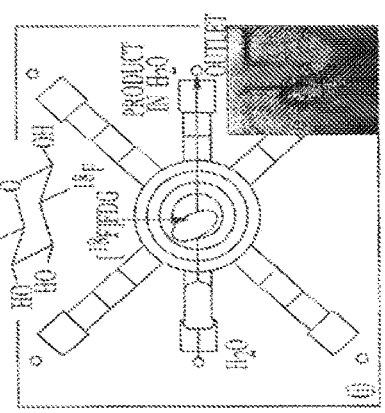
Fig. 9D
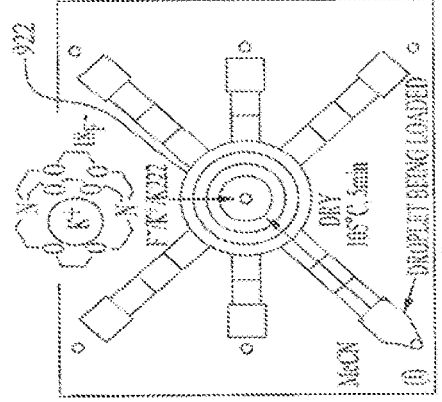
Fig. 9B
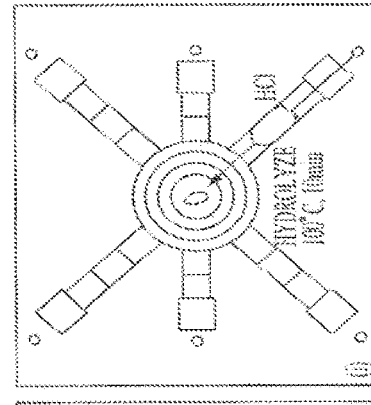
Fig. 9E
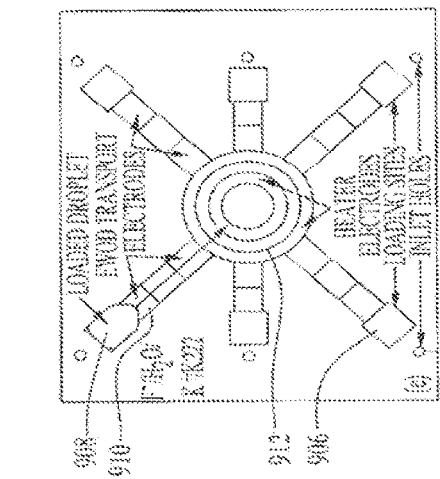
Fig. 9C
Fig. 9F

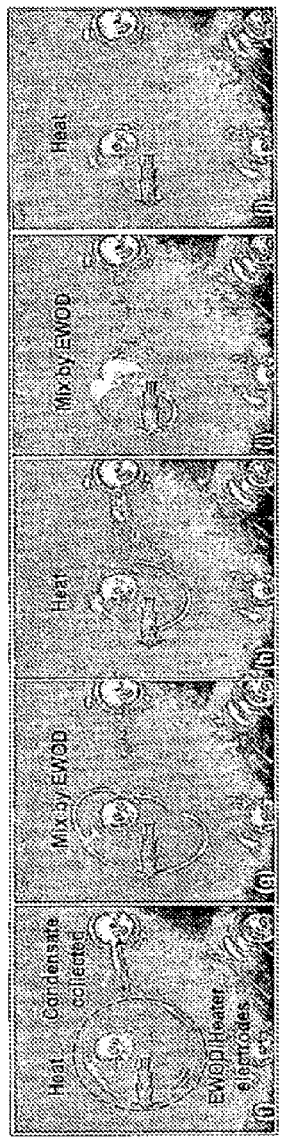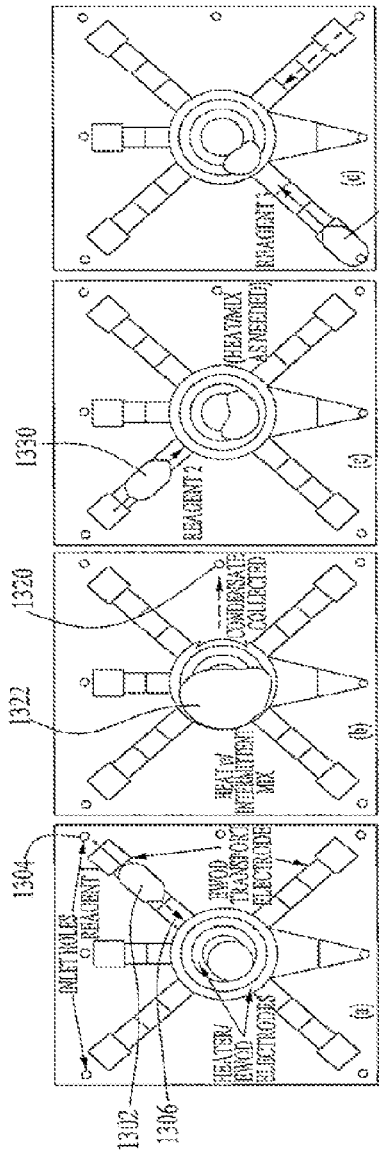

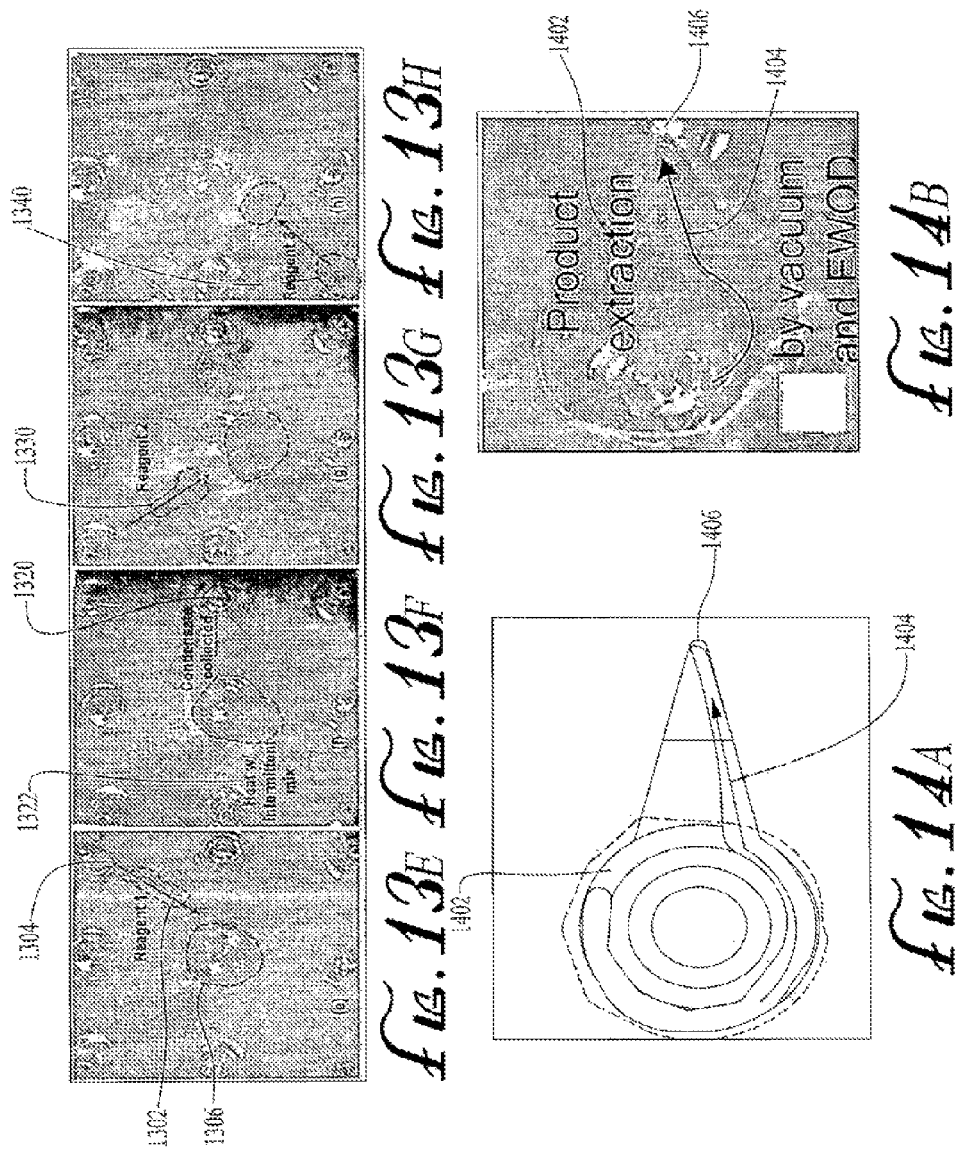

DISPOSABLE WORLD-TO-CHIP INTERFACE FOR DIGITAL MICROFLUIDICS

CROSS REFERENCE TO RELATED APPLICATIONS

This Application is a U.S. National Stage filing under 35 U.S.C. 371 of PCT Patent Application No. PCT/US2013/045030, filed Jun. 10, 2013, which claims priority to U.S. Provisional Patent Application No. 61/657,570, filed on Jun. 8, 2012. The contents of the aforementioned applications are incorporated by reference herein. Priority is expressly claimed in accordance with 35 U.S.C. §§119, 120, 365 and 371 and any other applicable statutes.

STATEMENT REGARDING FEDERALLY SPONSORED RESEARCH AND DEVELOPMENT

This invention was made with Government support under Grant No. DE-SC0001249 and and DE-SC0005056, awarded by the U.S. Department of Energy. The Government has certain rights in the invention.

BACKGROUND OF THE INVENTION

Field of the Invention

The present disclosure relates to a system, for example an automated system, for interfacing, processing, preparing, delivering to and/or collection of products from a micro-processing chip.

Description of the Related Art

A system performing sample preparation using cartridges (i.e. concentration of a solute from large 1 mL volume to small 5 uL volume using an anion exchange resin) has been used to interface with microfluidics. An example of such as system is set forth in Elisarov et al., J. Nucl Med 51(2): 282 (2010), which is hereby incorporated herein in its entirety by reference. However, this system utilized liquid valves, which resulted in the system being more expensive, the fluid path requiring cleaning rather than being disposable, and required the system to have larger size and larger surrounding apparatus.

Commercially available rotary valves with small volume injection loops have been used to achieve similar results to the above system, but still require much more space, undercutting the benefits of the microfluidics in the rest of the chemical processing system. Furthermore, these systems, however do not interface digital microfluidics chips, do not utilise electrowetting with solvent exchange, and do not utilize an integrated platform for digital microfluidics or a purely liquid-valve free system.

Reagents utilized with the above mentioned systems are typically loaded manually to the chip, leading to chemical and radiation exposure hazards, and require greater time, effort and expertise. The common approach of pre-loading reagents into on-chip or off chip reservoirs is not feasible for this application due to volatility of many reagents, concerns of cross-contamination, and the possibility of being incompatible with certain organic solvents.

Some automated extraction of product from a digital microfluidics chip into a capillary for nanospray injection has been reported, for example, by Shin et. al, (Anal. Chem. 2012, 84, 3731-3738, which is hereby incorporated herein in its entirety by reference) by introducing a glass capillary into the gap between chip substrates. Liquid was removed from the chip using the capillary effect in the inside walls of the capillary, and was ejected by applying 1.7-2.2 kV of potential, which creates a nanospray. Other approaches to removal of products/droplets from chips includes bringing the liquid droplet in contact with another preferentially wetting surface (See Yi, Sensors and Actuators, 2004, 114 (2-3), 347-354, which is hereby incorporated herein in its entirety by reference). However, one of the disadvantages of these approaches is that they are not suitable for applications where the collected product needs to be further processed for more synthesis steps, purification or quality control before use, as is commonly required from chemical synthesis products, especially those for use in biological systems.

SUMMARY

Embodiments incorporating features of the present invention include interfaces, such as disposable and/or automated interface systems, capable of on-demand delivery from multiple organic and inorganic liquids to a digital microfluidics chip, as required for organic chemistry.

In some embodiments, the proposed interface leverages the infrastructure of a microfluidic chip devices with very few additional components and systems needed to provide interfaces for sample preparation, introduction, purification and collection.

Although chemistry on digital microfluidics has been performed using manual interfacing (e.g. pipetting) with the chip for preparation, loading and collection operations, embodiments incorporating features of the present invention describe a compact, automated, integrated platform that interfaces with the chip upstream and downstream of the reaction, as well as between intermediate reaction steps if needed. Some embodiments utilize no active wetted components in this interface allowing a single-use disposable cassette based system which does not require any wash steps between reactions.

A significant advantage of the invention is its automation. As a result of automation, the platform (to carry out microscale chemical reactions, for example) is easier to use, requires less skill to operate, and human error is eliminated. Furthermore, repeatability of processes is increased. Additionally, if the chemical process involves hazardous or sensitive reagents or reactions (e.g. radioactive isotopes), it can be placed in an appropriate shielding or containment without hindering operation as would foe the case for a manually operated system.

These and other further features and advantages of the invention would be apparent to those skilled in the art from the following detailed description, taking together with the accompanying drawings, wherein like numerals designate corresponding parts in the figures, in which:

BRIEF DESCRIPTION OF THE DRAWINGS

FIG. 3A depicts a schematic representation of a elec-trowetting-on-dielectric based compact synthesizer incorporating features of the present invention;

FIG. 3B depicts an enlarged view of a microfluidic chip that can be utilized with the synthesizer depicted in FIG. 3A;

FIG. 4 a schematic representation of one embodiment of a method incorporating features of the present invention;

FIGS. 5A-5F depict several steps of a schematic representation of the setup and operation of the automated injection interface incorporating features of the present invention;

FIG. 6 is a graphical representation of signals from the liquid sensors LS1 and LS2 shown in the embodiment depicted in FIGS. 5A-5F;

FIG. 7 is a graphical representation of verification of the process depicted in FIGS. 5A-5F;

FIGS. 9A-9F are schematic representations of one embodiment of a method incorporating features of the present invention;

FIGS. 12A-12J depict an image sequence showing multiple droplet loading followed by heating with intermittent mixing, corresponding to the graphical representation in FIG. 11 above;

FIGS. 13A-13D show a schematic representation of a multi-reagent loading and heating with mixing incorporating features of the present invention;

FIGS. 13E-13H show an image sequence showing multi-reagent loading and heating with mixing that corresponds respectively to FIGS. 13A-13D above;

FIG. 14A is a schematic view of extraction electrodes incorporating features of the present invention;

FIG. 14B is a top image view of the extraction electrodes depicted in FIG. 14A above;

DETAILED DESCRIPTION

Figure 1:
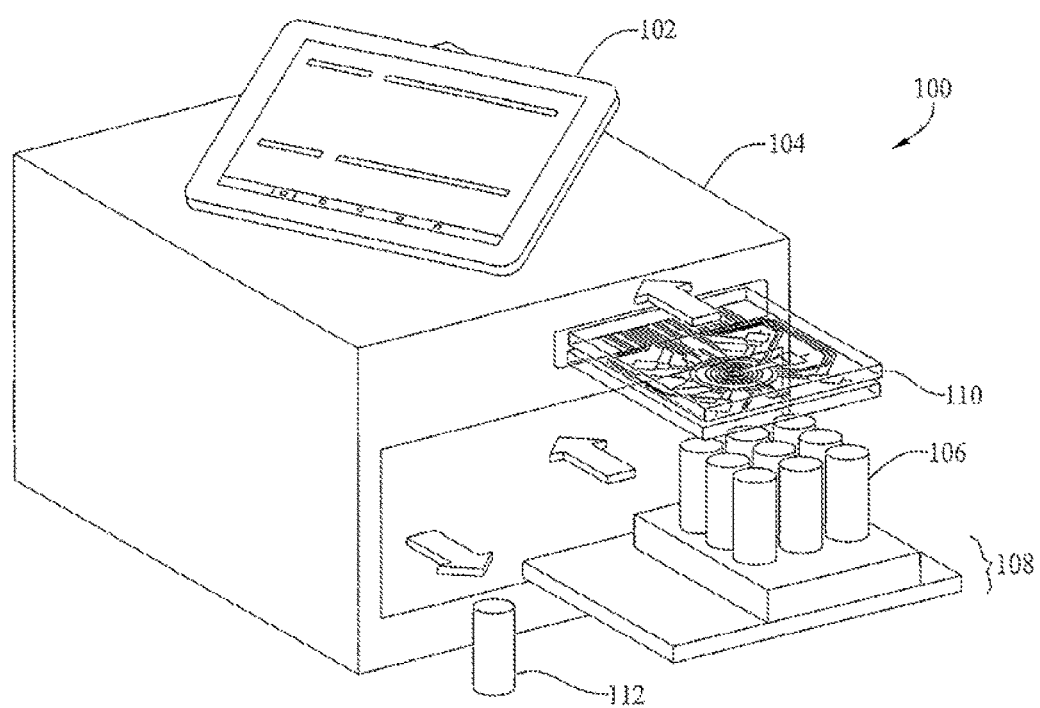
FIG. 1 depicts an example platform for utilization of methods incorporating features of the present invention.

In some embodiments incorporating features of the present invention, compact, automated, integrated platforms were utilized that interface with a chip upstream and downstream of the reaction, as well as between intermediate reaction steps if needed. In the various embodiments disclosed many different arrangements are possible which provide automated operation of the interface, including automation of a multiple reagent process.

Throughout this disclosure, the preferred embodiments herein and examples illustrated are provided as exemplars, rather than as limitations on the scope of the present disclosure. As used herein, the terms "invention," "method," "system," "present method," "present system" or "present invention" refers to any one of the embodiments incorporating features of the invention described herein, and any equivalents. Furthermore, reference to various feature(s) of the "invention," "method," "system," "present method," "present system," or "present invention" throughout this document does not mean that all claimed embodiments or methods must include the referenced feature(s).

It is also understood that when an element or feature is referred to as being "on" or "adjacent" another element or feature, it can be directly on or adjacent the other element or feature or intervening elements or features that may also be present. Furthermore, relative terms such as "outer", "above", "lower", "below", and similar terms, may be used herein to describe a relationship of one feature to another. It is understood that these terms are intended to encompass different orientations in addition to the orientation depicted in the figures.

Although the terms first, second, etc. may be used herein to describe various elements or components, these elements or components should not be limited by these terms. These terms are only used to distinguish one element or component from another element or component. Thus, a first element or component discussed below could be termed a second element or component without departing from the teachings of the present invention. As used herein, the term "and/or" includes any and all combinations of one or more of the associated list items.

The terminology used herein is for the purpose of describing particular embodiments only and is not intended to be limiting of the invention. As used herein, the singular forms "a," "an," and "the" are intended to include the plural forms as well, unless the context clearly indicates otherwise. For example, when the present specification refers to "a" transducer, it is understood that this language encompasses a single transducer or a plurality or array of transducers. It will foe further understood that the terms "comprises," "comprising," "includes" and/or "including when used herein, specify the presence of stated features, integers, steps, operations, elements, and/or components, but do not preclude the presence or addition of one or more other features, integers, steps, operations, elements, components, and/or groups thereof.

As used herein the term "vial" is used as a generic term describing any container of any material which can be sealed to retain positive or negative pressure, such as a glass vial or a reservoir in an integrated injection molded plastic part (possibly having multiple reservoirs and other features), and into which one or more tubes can be pierced through a penetrable surface such as a septum or a sealing tape. The size, shape and materials can be chosen as suitable for the application.

As used herein, "tubes" or "tubing" is used as a generic term describing fluid pathways across the interface from world-to-chip. It refers to any kind of fluidic conduit or pathway made from metallic or non-metallic materials such as steel, stainless steel, aluminum, PEEK®, Teflon®, Ultem®, silicone, polyurethane, etc. The tubing can be of any cross-section such as circular, square, or arbitrary shape. Some or ail of the length of the fluid pathways can be formed by etching glass, silicon, or plastics, or molding materials such as plastics into two-dimensional or three-dimensional forms, or by placing two or more surfaces of each material adjacent so one another so as to form a fluidic path or provide fluid channels by a laminated structure. The fluid pathway can also be provided by a wicking structure, such as provided by a fibrous material along which a fluid can flow or foe transmitted, either passively or actively.

Embodiments of the invention are described herein with reference to different views and illustrations that are schematic illustrations of idealized embodiments of the invention. As such, variations from the shapes of the illustrations as a result, for example, of manufacturing techniques and/or tolerances are expected. Embodiments of the invention should not be construed as limited to the particular shapes of the regions illustrated herein but are to include deviations in shapes that result, for example, from manufacturing.

Before explaining embodiments incorporating features of the present invention in greater detail, it is useful to first describe an example environment of an interface in which these embodiments can be applied. FIG. 1 shows an example platform 100 utilizing using a world-to-chip interface incorporating features of the present invention. This example platform comprises an interface 102, such as a computer, and a functional body 104 configured to accept one or more reagents 106, which can be organized into a consumables kit arrangement 108, and can further accept a digital microfluidic chip 110. After formation of the desired product, the product can be retrieved from the platform 100, for example, via a product collection vial 112.

Figure 2A:
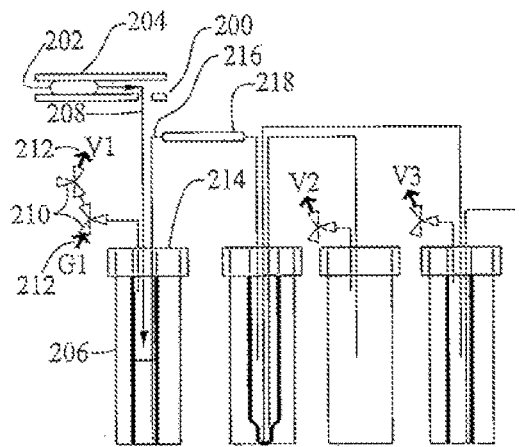
FIGS. 2A-2D depict schematic representations of one embodiment of a method incorporating features of the present invention.

In some embodiments, an interface to a two-substrate digital microfluidic chip, a commonly used configuration of digital microfluidic chip, performs reactions in the gap between the two substrates. As shown in FIG. 2A, which demonstrates the step of extracting a desired product from a microfluidic chip 200, droplets of liquid reagents and reaction products 202 are sandwiched between the two substrates 204. It is important to note that liquid reagents are not the only phase of reagents that can be utilized. Gas-phase reagents can also be introduced, for example, in the medium around the droplets, and solid-phase reagents and supports can been used on the chip. A sealable container 206, such as a vial, can be positioned and connected to the gap between the two substrates through a conduit 208, such as tubing. "Sealable vial" as used herein is a generic term describing any container of any material which can be sealed to retain positive or negative pressure, and into which one or more tubes can be placed, preferably by piercing through a penetrable surface such as a septum. A common vial as contemplated herein is glass with rubber-containing septum.

Pressure in the vial can be applied via tubing connected to switchable gas valve(s) 210 thus connecting the vial to a regulated pressure source 212, such as a vacuum source or regulated positive-pressure source. This arrangement can provide atmospheric pressure to the vial or block airflow to and from it, which allows the contents of the vial to be delivered and moved as needed to perform various processes, some of which are described below. It is important to note that these valves never come into contact with the liquid contents placed in the vial; the use of gas provides a 'contact-less' means of delivering solutions. The described interface can contain a multiplicity of such vials, connected directly or indirectly to the chip through tubing and/or other vials. By using one or more controllable gas valve(s), a controllable positive-pressure source and a controllable vacuum source, through which no liquid passes, one can accurately control the pressure inside each vial, and hence whether liquid flows in or out of it.

The vial septum 214 can be pierced, or otherwise accessed, by one or more fluid pathways 216, such as tubing, with ends located at remote distances from the septum surface. In the case of upright vials, gas tubing and tubing that delivers liquid into the vial has a delivery end closer to the septum on top (i.e. above the surface of any liquid that is present in the vial); those that remove liquid from the vial tend to reach down further into the vial (i.e. to the bottom or at least below the liquid surface) so as to access the intended liquid contents. However, this arrangement can be reversed for inverted vials.

A combination of pressure and vacuum can be used to deliver liquid from one vial to the chip or to another vial, or from the chip into a vial and back to the same chip or to another chip. Furthermore, any of the fluid pathways 216 from one vial to another may contain passive elements 218 for processing the liquid, for example, they may contain inline filters or purification cartridges to trap impurities or to trap the compound of interest (which could then be later elated off of the cartridge with suitable eluent, as will be discussed further below). The filters or purification cartridge material can be packed into inexpensive tubing, which either directly penetrates the vial septum, or can be connected to the septum penetrating tubing in such a way as to avoid product loss or volume loss at the interface. As an example, a metal or polymer tubing with outer diameter to snugly fit through an opening in the septum or inside a metal or polymer tubing that functions as the penetrating tubing and/or the cartridge/filter containing tubing, respectively or vice versa.

The implementation of the on/off valve function of flow from or to a vial is an alternative and not necessary to utilise methods incorporating features of the present invention. In some embodiments, a "selector valve" function can be implemented where liquid from one of two or more sources can be selectively delivered to one receptacle, or liquid from one source can be delivered to one of multiple receptacles (as shown in FIG. 2A). For example, a tubing 208 may terminate in one vial, and then this vial may contain one or more dip tubes 216 going to another vial with a controlled vacuum source in each. By selectively controlling which secondary vial has vacuum applied, the liquid from the tubing can be directed into one or the other of the secondary vials.

In each case, both the receptacle and source can be embodied as either a vial or a chip, with the difference being that a chip is typically open to atmosphere while a vial can be pressurised or evacuated. With well-controlled pressure and vacuum, and choosing the right depths to which tubing penetrates into the vials, one can achieve virtually any fluidic routing without the use of liquid valves and only wetting inexpensive components like tubing and vials. These tubes and vials can fluidically interact with the digital microfluidic chip and can comprise a disposable cassette. Moreover, by using the appropriately sized vials and tubing, even inexpensive commercially available vials and tubing, the entire system can be fit with a large number of vials within footprints comparable to typical digital microfluidics chips (e.g. ~1-2"×1-2"). As an alternative, the vials and related components described above can be provided as a single integrated molded plastic unit comprising multiple vials and necessary connecting tubing.

Another feature that can be achieved is the controlled amount of liquid delivery from a source to a receptacle. By carefully controlling the applied pressure, vacuum or both and the appropriate valve actuation timing, at both the source and receptacle, one can also meter a desired amount of liquid and deliver that liquid from the source into the receptacle. The process can be aided by feedback sensors such as, but not limited to, a liquid sensor, a level detector, a weighing scale, an electrical sensor, an electrochemical sensor, a radiation sensor, an acoustic sensor, an optical sensor etc., or can be based on timing-based actuation. As a subset of the feedback controlled process, the feedback can be obtained on the digital microfluidic chip through electrical means, any other means listed above, or a different mechanism.

As an illustration of the capability of such an interface, and methods utilizing such an interface incorporating features of the present invention, a cartridge purification operation can start with a droplet containing a species of interest (e.g. a crude reaction mixture such as a desired intermediate or final product mixed with impurities and byproducts) placed in the gap between the two substrates. First, as shown in FIG. 2A, product from the chip 200 is collected or extracted into a vial 206 by applying vacuum into the "Extract" vial 206. More liquid can be added into the chip, for example, more solvent to rinse the surface of the chip, or more product that was previously collected in a vial, by applying well-controlled pressure to that source vial (not shown in figure as that source vial is part of a reagent preparation and loading interface).

Figure 2B:
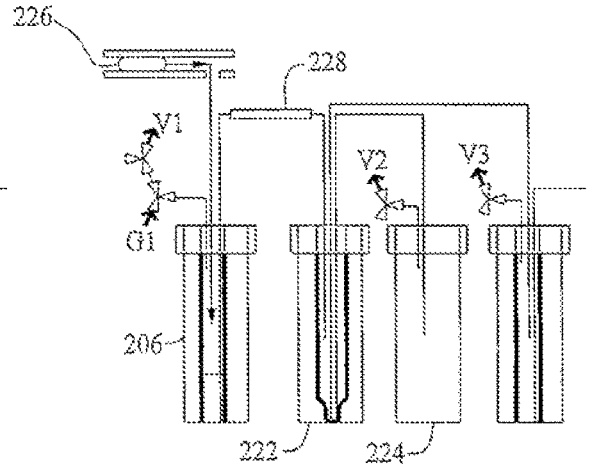

Next, as shown in FIG. 2B, liquid from the pressurized "Extract" vial 206 was pumped through a purification cartridge 228 into a "Onion" vial 222 from where it is subsequently pulled into a "waste" vial 224 by applying vacuum to the latter. The cartridge provides a size or affinity based separation, for retaining the species of interest while the impurities pass through. Alternatively, the cartridge can be a filter assembly. The steps shown in FIGS. 2A-2B and discussed above can be repeated multiple times and from multiple sources. Once all the required products were trapped on the cartridge or filter 228, a small amount of eluent 226 could be delivered either through the chip or directly from another vial (not shown in figure) via separate tubing, into the "Extract" vial 206.

Figure 2C:
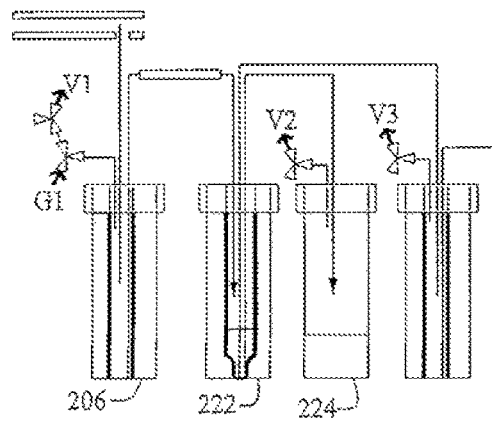
Figure 2D:
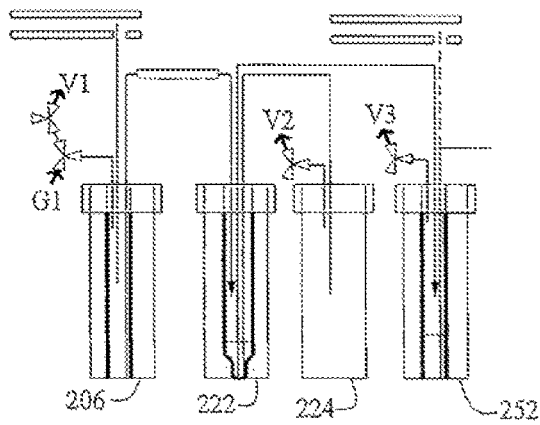

The delivery of eluent is shown in FIG. 2C. The volume of the eluent introduced can be metered as stated above, controlled by the appropriate choice of pressure, vacuum and valve actuation, and using feedback or timing based control. Similar to the step depicted in FIG. 2B, liquid can be pumped out of the "Extract" vial 206, into the "Union" vial 222 but this time, as shown in FIG. 2D, vacuum can be applied to a "Pure" vial 252 instead of the "Haste" vial 224 so as to collect the elated product in the "Pure" vial 252. Depending on whether this was the final purification step, or an intermediate step before further on-chip steps, liquid can be routed appropriately. For instance, liquid could be pumped to a quality control (QC) system, to a different location on the same chip, a separate chip, or to another vial or system.

It has been shown, according to the present disclosure, that by using the appropriate choice of vial sizes as well as the volumes used for various steps, one can use the interface described above to bridge the gap between the macroscale world (e.g. hundreds of microliters to several mL) and the microscale digital microfluidic chip volumes (e.g. 1 to 20-30 microliters).

In one embodiment according to the present disclosure, a user-friendly, self-shielded, bench/top radiosynthesizer using electrowetting-on-dielectric (EWOD) microfluidic chip technology is disclosed that would eliminate reliance on centralized radio-pharmacies and enable diverse PET probe production in clinics and research labs. While tiny reagent droplet volumes (<20 μL) can be controlled entirely electronically on digital microfluidic chips, known methods involve numerous manual operations that would lead to avoidable radiation exposure and complexity in a production environment. Disclosed herein are compact, automated, multi-reagent loading systems to load reagents to the chip from septum-capped reservoir vials. A challenge exists in how to load a sufficient quantity of the radioisotope onto the chip for synthesis. Methods incorporating features of the present invention can integrate a module to pre-concentrate [F-18]fluoride so a controlled amount of activity from a ~1 mL source vial (e.g. from a cyclotron or radio-pharmacy) can be loaded into a ~20 μL reaction volume of the chip.

While preserving compactness and the separation of wetted and non-wetted components, a pre-concentration module was built into a multi-reagent loading and extraction system. The desired volume (and activity) from the source vial is pneumatically delivered to the system. A combination of pressure and vacuum valves was used to trap the [F-18]fluoride on a quaternary methyl ammonium (QMA) column, and release with a fixed volume (~20 μL) of eluent containing $K_2CO_3$ and Kryptofix for loading to the chip.

In one embodiment, starting with a significant volume fraction (~0.3-0.5 mL) of [F-18]fluoride from the contents of the source vial (~1 mL), fully automated trapping of F-18 with high efficiency (96±6%, n=6) and release with ~20 μL of eluent with high overall efficiency (89±7%, n=6) was achieved. These results in on-demand, fully automated high-efficiency pre-concentration into microfluidic-compatible volumes are demonstrated in a fashion amenable to a disposable kit model for PET probe production.

Shown in FIG. 3A is a schematic workflow 300 for one embodiment of a benchtop electrowetting-on-dielectric based compact synthesiser 301. Using a pre-concentration module integrated into the reagent loading and extraction system, crude [F-18]fluoride from the source vial 302 (e.g. received from the radio-pharmacy 304) is concentrated via a pre-concentration module 306 into a volume deliverable to the EWOD chip 308. Cold reagents 310 can also be delivered to the EWOD chip 308. In one embodiment, the volume is a 20-uL reaction volume. After on-chip synthesis, the extracted product is collected in a collection vial 312 is then purified and quality-checked via a purification QC step 314 before the injection step 316. The synthesiser comprises a fluidic interface 318 and a portion arrangeable to receive input, such as product and reagents, for example, from vials and/or cassettes 320. FIG. 3B shows an enlarged view of an EWOD chip 308.

In one embodiment, an automated "chip-to-world" interface between an electrowetting-on-dielectric (EWOD) digital microfluidic device 308 and high-performance liquid chromatography (HPLC) system, expanding the application of previous EWOD chemical synthesis devices to syntheses that require HPLC purification is disclosed. The interface collects the crude product from the chip without the need for chip disassembly or other manual intervention. Some advantages of this method include: 1) a bubble-free filling of the injection loop; 2) a quantification of how much crude product from the chip is loaded into the loop; and 3) a successful injection and HPLC purification of a crude product. It should be noted that because of the small chip volume, analytical-scale HPLC can be used, leading to 10-20× more concentrated purified product, than semi-preparative HPLC. An overview of this process is shown in FIG. 4, which depicts the automated micro-injection interface 402 providing an interface between the EWOD chip and HPLC purification. FIG. 4 shows the general process flow of a step of performing microchemical synthesis on a digital microfluidic chip 404 utilising the interface 402 to perform the step of purification with analytical scale HPLC 406 to achieve a final purified product 408

FIGS. 5A-5F illustrates the setup and operation of the automated injection interface. First, a vacuum was applied to collect product from the EWOD chip 502 into the "Extract" vial 504. An example of this procedure is set forth in G. J. Shah, et al., Intl. Symposium on Microchemistry and Microsystems, Zhubei, Taiwan, June 2012, which is hereby incorporated herein in its entirety by reference. To eliminate bubbles that are undesirable in HPLC, the contents are pushed into the "degassing" vial 506 and weak vacuum applied (this step is shown in FIG. 5B). Degassed liquid is pulled into the loop by applying vacuum at the "Overflow" vial 508 (shown in FIG. 5C). When the loop is unfilled, as indicated by the liquid sensors LS1 512 and LS2 514, the rotary valve 516 was switched to stop injection of bubble-free liquid. (FIG. 5D). When the loop 510 is filled, as sensed by the liquid sensors 512, 514, the rotary valve 516 is switched to inject the bubble-free liquid in the loop into the HPLC column (FIG. 5E).

FIG. 5F shows a schematic overview of the above automated process. FIG. 5F depicts that liquid is moved to the outlet hole using the EWOD 502 and collected with vacuum into the "Extract" vial. To remove air bubbles, liquid was then pushed using compressed gas from the extract vial 504 into the "degassing" vial 506, where a weak vacuum is applied at the top. Liquid is then pulled from the degas vial using the vacuum applied to the "overflow" vial 508, across LS1 512 into the injection loop on the rotary valve 516 and LS2 514. Once liquid fills the loop as indicated, by LS1 and LS2, the vacuum is turned off and the rotary valve 516 is switched to inject the loop's contents into the purification column. The entire process can be automated by software-controlled EWOD actuation, vacuum and pressure using timing and electronic feedback.

FIG. 6 is a graphical representation of signals from the liquid sensors LS1 512 and LS2 514, as discussed above in relation to FIGS. 5A-5F, that flank the injection loop during liquid filling. First, the solution containing crude product is collected from the chip 502, degassed and transferred towards the loop until LS1 512 is activated (~25 s on plot). Additional solvent is then added to rinse the tubing and the two vials upstream of the loop, following which transfer is resumed to completely fill the loop such that the liquid reaches LS2 514 (~100 s on plot). The flat trace 602 of the LS1 502 during loop filling indicates absence of bubbles in the loop.

Radioactive [$^{18}$F]fluoride in water was used to quantify volume loss between the chip and the loop. Approximately 65 µL of radioactive sample was first passed through the interface and loaded, until LS1 was activated. (In this state, the degassing vial still contains liquid, but the tubing between the vial and LS1 was filled.) Next, ~65 µL of water was loaded onto the chip to rinse out residual activity along the lines and tubing and transfer from the degassing vial was resumed until LS2 was activated. Radioactivity outside the loop (upstream and downstream), and loaded into the loop were separately measured. Approximately, 82±4% of the starting activity was found to be loaded into the loop, which is similar or better than typically achieved with manual collection from the EWOD chip.

As a verification of the process, crude [$^{18}$F]fallypride (a PET tracer that measures dopamine D2/D3 neuroreceptors) was injected from an on-chip radiochemical synthesis through the interface into the HPLC column and distinct peaks were obtained for the main product and side-products. As shown in FIG. 7, peaks 702 were collected in separate fractions enabling isolation of pure [$^{18}$F]fallypride. These results demonstrate a practical interface for automated injection from an EWOD chip to an HPLC purification system. To miniaturize the overall chemical synthesis and purification system, methods incorporating features of the present invention can be extended to exploit smaller-scale HPLC columns (e.g. L. A. Colon, et al., Analyst, 2004, 129, pp. 503-504, which is hereby incorporated herein in its entirety by reference.) and systems (e.g. D. S. Reichmuth, et al., Anal. Chem. 2003, 77, 2997-3000, which is hereby incorporated herein in its entirety by reference). Although useful for all chemical and biochemical synthesis due to ease of operation and reduced chemical hazard, the automation has the additional benefit for radiochemistry of minimizing radiation hazards.

In some embodiments incorporating features of the present invention automated radiosynthesis and HPLC purification of [$^{18}$F]fallypride are discussed and verify the functionality of radiochemistry platforms based on electrowetting-on-dielectric (EWOD) digital microfluidics. Using purely electronic control and no moving parts, reagents in the form of droplets (typically ~1-25 µL) can be sequentially moved, mixed and reacted at high temperatures on the EWOD micro-reactor to perform radiosynthesis.

Proof of concept experiments of radiosynthesis on EWOD chip relied on manual pipetting of reagents to the chip and manual collection of the synthesized product from the chip. Methods according to the present disclosure include a technique for reagent loading, providing automated and controlled delivery of multiple aqueous and non-aqueous reagents from septum-capped reservoir vials to the chip. The present disclosure also demonstrates the automated concentration of [$^{18}$F]fluoride radioactivity in [$^{18}$O]water from the cyclotron from ≥100 µL to ~20-50 µL which is a volume small enough for delivering most of the activity to the chip. Additionally, for probes that require purification by HPLC, the present disclosure describes an injector interface to collect the product from on-chip synthesis and inject it into an HPLC purification system. Using the techniques described herein with [$^{18}$F]fluoride added to water, ~82±4% of the liquid from the chip was delivered into the injection loop.

Embodiments according to the present disclosure integrate all of the above components into a system and as a proof of concept demonstrate the synthesis of [$^{18}$F]fallypride. Radiosynthesis of [$^{18}$F]fallypride on an EWOD chip was demonstrated with repeatable and high fluorination conversion (86±8%, n=5) [4]. Similar results were achieved with automated synthesis. Following automated synthesis, the crude product is automatically injected into an analytical-scale HPLC for purification to obtain purified [$^{18}$F]fallypride.

The entire system can utilize inert gas (pressure and vacuum) to transfer liquids through inexpensive wetted components (i.e., tubing, needles and vials) that are well-suited to be part of a disposable cassette model. All fluidic operations on-chip and off-chip are performed remotely through software, reducing time, labor and exposure hazards from chemicals and radiation. All components of the system that require radiation shielding, namely the concentrator, reagents cartridge, microfluidic chip and HPLC injector, are highly compact (fit within a 20×15×15 cm$^3$ volume) suggesting the feasibility of a benchtop, self-shielded radiosynthesizer.

Figure 8A:
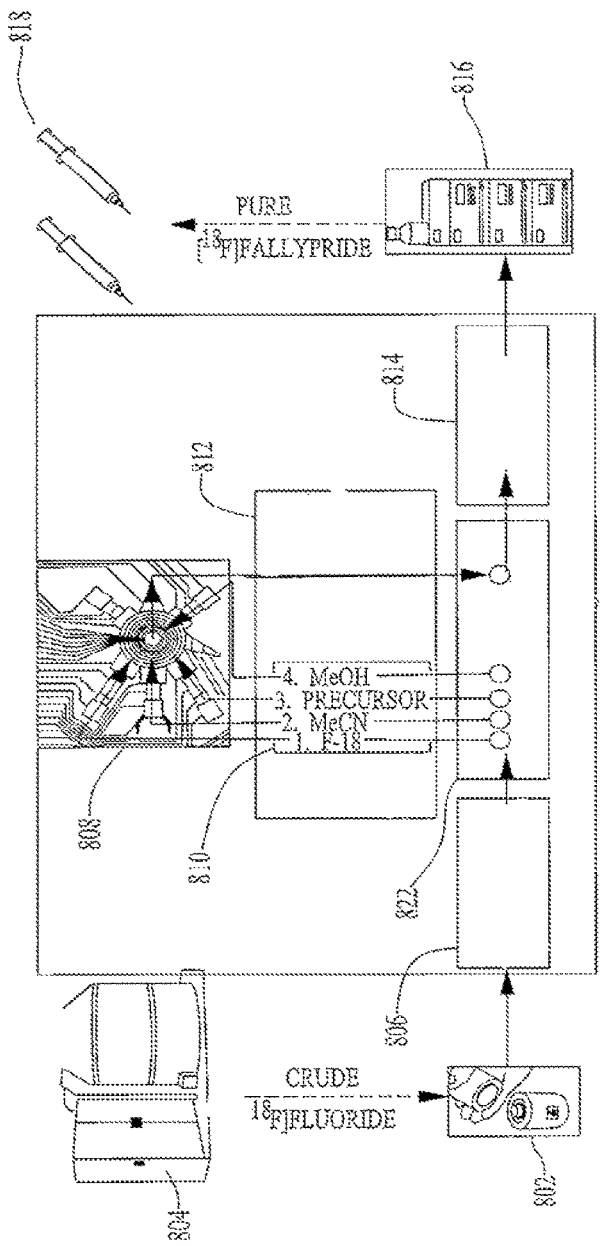
FIG. 8A depicts a schematic of an embodiment of an automated radiochemistry platform incorporating features of the present invention.
Figure 8C:
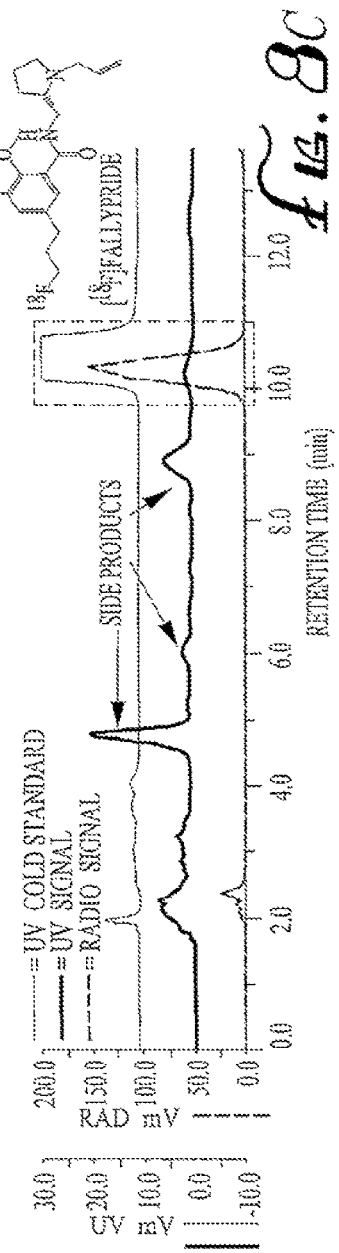
FIGS. 8B-8C depict graphical representations of results of tests conducted in regard to the embodiment depicted in FIG. 8A.
Figure 8B:
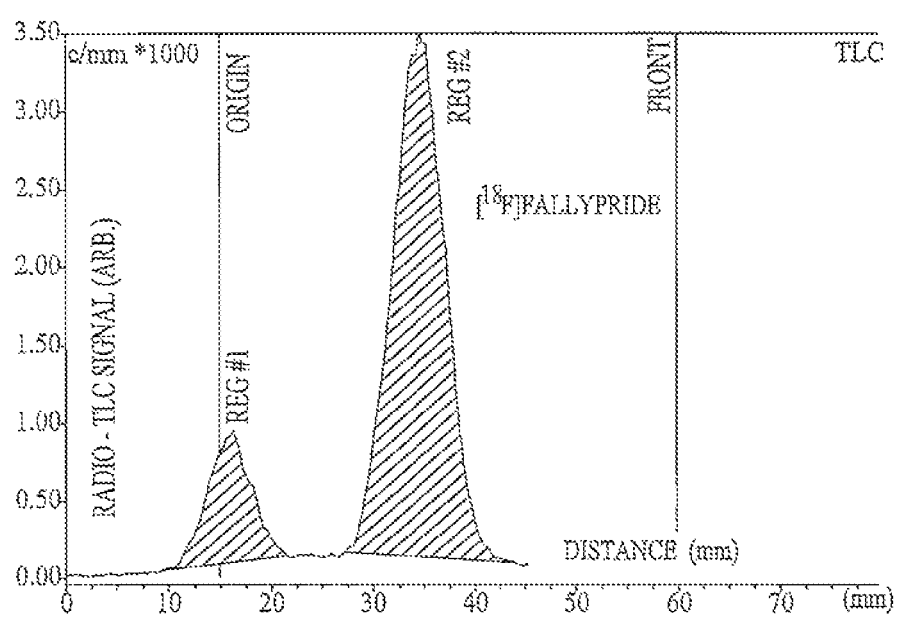

FIG. 8A shows a schematic of an embodiment of an automated radiochemistry platform incorporating features of the present invention, similar to the processes represented by FIGS. 5A-5F, 8 and 7. Crude [$^{18}$F]fluoride 802 from a cyclotron 804 is concentrated in a concentration step 806 and delivered to the chip 808, along with other cold reagents 810 supplied from the reagents cartridge 811. For [$^{18}$F] fallypride, azeotropic drying (105° C.) with acetonitrile (MeCN) was performed using concentric ring-heaters on the chip. Next, the precursor was added and fluorinated at 100° C. The crude product was dissolved in methanol (MeOH) and extracted into a vial in an extraction step 812. It was then degassed and injected during an injection step 814 into the HPLC 816 for purification where it was further subjected to a subsequent QC step 818. As shown in FIG. 8B, the radio-TLC of the crude product indicates good conversion (86±8%). As shown in FIG. 8C, the HPLC outpost shows good separation of pure [$^{18}$F]fallypride from side-products.

The present disclosure sets forth further embodiments of automated systems for the radiochemical synthesis of [$^{18}$F] FDG (FDG) using an EWOD digital microfluidic chip. EWOD provides a more robust and reliable platform for radiosynthesis than other microfluidics platforms for batch radiosynthesis due to the inert Teflon® surface compared to POMS which absorbs or interacts with organic solvents and reagents. Additionally, liquids are controlled entirely electronically providing flexibility in synthesis protocols and additional robustness. Repeatable synthesis of FDG sufficient for preclinical imaging on EWOD devices has been achieved with high fluorination efficiency (88±7%, n=11) and high hydrolysis efficiency (>95%, n=9). Following radiosynthesis, off-chip purification through a miniaturised cartridge produced high purity (>99%) FDG.

The system, provides automated loading of all the reagents for FDG synthesis on an EWOD. As shown in FIG. 9A, the EWOD chip 902 (which can be approximately 5×5×0.3 cm$^3$) contains an array of inlet ports 904 located to match the liquid delivery needles held in a needles block, connecting the chip to the vials in the vials holder. Each vial also has a gas delivery needle connected through channels in the needle block to pneumatic valves, so as to enable independent loading from any vial. Each inlet port 904 on the chip is adjacent to a loading site 906, where an EWOD electrode is used to electrically sense the arrival of liquid. Once loaded, droplets 90B can be transported by sequential application of EWOD voltage to the appropriate transport electrodes 910. The EWOD chip contains a reaction site 912 comprising concentric ring-shaped electrodes for resistive heating to perform reactions and evaporations.

FIGS. 9A-9F illustrates the steps of the FDG synthesis as performed on an EWOD chip, where reagents are loaded in sequence at loading sites, transported by EWOD, and heated at the central heater for the drying, fluorination and hydrolysis steps. The final product, (the chemical formula for FDG is shown in FIG. 9F) is extracted for in-line purification. All components requiring radiation shielding are highly compact (fit within a 15×10×10 cm$^3$ volume) and is therefore suitable for a bench top radiosynthesis system.

The electrode surfaces 910 are initially hydrophobic. When EWOD actuation voltage is applied to the electrode, the electrode surfaces 910 become hydrophilic, causing droplet transport. After voltage was turned off, the surface returns to hydrophobic and droplet transport ceases. Each vial cap is punctured, or otherwise accessed, by a liquid delivery needle connected to the chip, and a gas delivery needle, connected to a pneumatic valve (not shown) through a gas channel.

FDG synthesized on an EWOD was used to image BC-1 lymphoma xenograft in a mouse. Biodistribution was very similar to [$^{18}$F]FDG from conventional radiopharmacy. FIGS. 9A-9E illustrate the automated radiosynthesis on EWOD. FIG. 9A shows liquid pumped into the chip through inlets adjacent to loading sites. FIG. 9B shows loaded droplets transported by an EWOD to the heater 922 for drying. FIG. 9C shows mannose triflate added to the reaction site 912. As shown in FIG. 9D, the droplets were then reacted with the mannose triflate at 120° C. for ~10 minutes. As shown in FIG. 9E the droplets were then hydrolyzed with hydrochloric acid at 100° C. for ~10 minutes. Finally, FIG. 9F shows the production of [$^{18}$F]FDG 960 which can be extracted with water for off-chip purification.

Chemical reactions typically require non-aqueous (organic) reagents, posing significant technical challenges for digital microfluidics using EWOD. Although less common than aqueous liquids, on-chip droplet manipulation of organic liquids on an EWOD has been utilized. Previously reported methods typically used for storage and automatic dispensing of aqueous reagents on an EWOD, however, were not suitable for organic media. These reagents are often volatile and/or sensitive to air/moisture (rendering on-chip storage impractical), and tend to be wetting even on fluoropolymers (hence prone to uncontrolled chip-flooding). However, utilising compressed inert gas and gravity, the present disclosure describes a versatile liquid dispensing technique for dispensing micro-droplets of such liquids (including organic solvents) from sealed off-chip reservoirs that prevents environmental contamination during storage, avoids flooding during loading and requires no carrier fluid or moving parts.

Figure 10A:
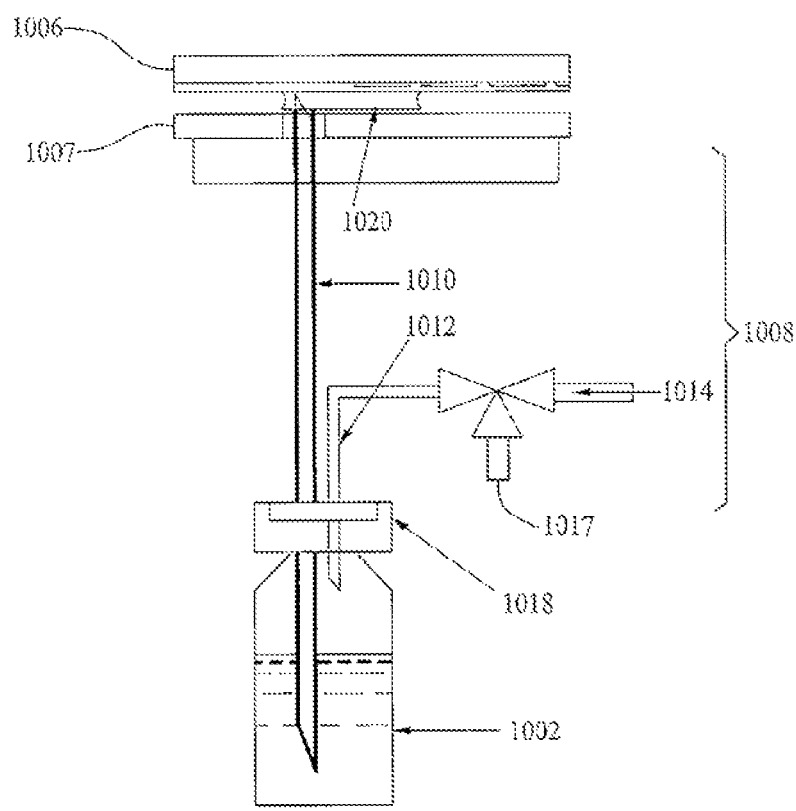
FIG. 10A is a schematic representation of one embodiment of a multi-reagent, loading setup for aqueous and non-aqueous reagents incorporating features of the present invention.
Figure 10B:
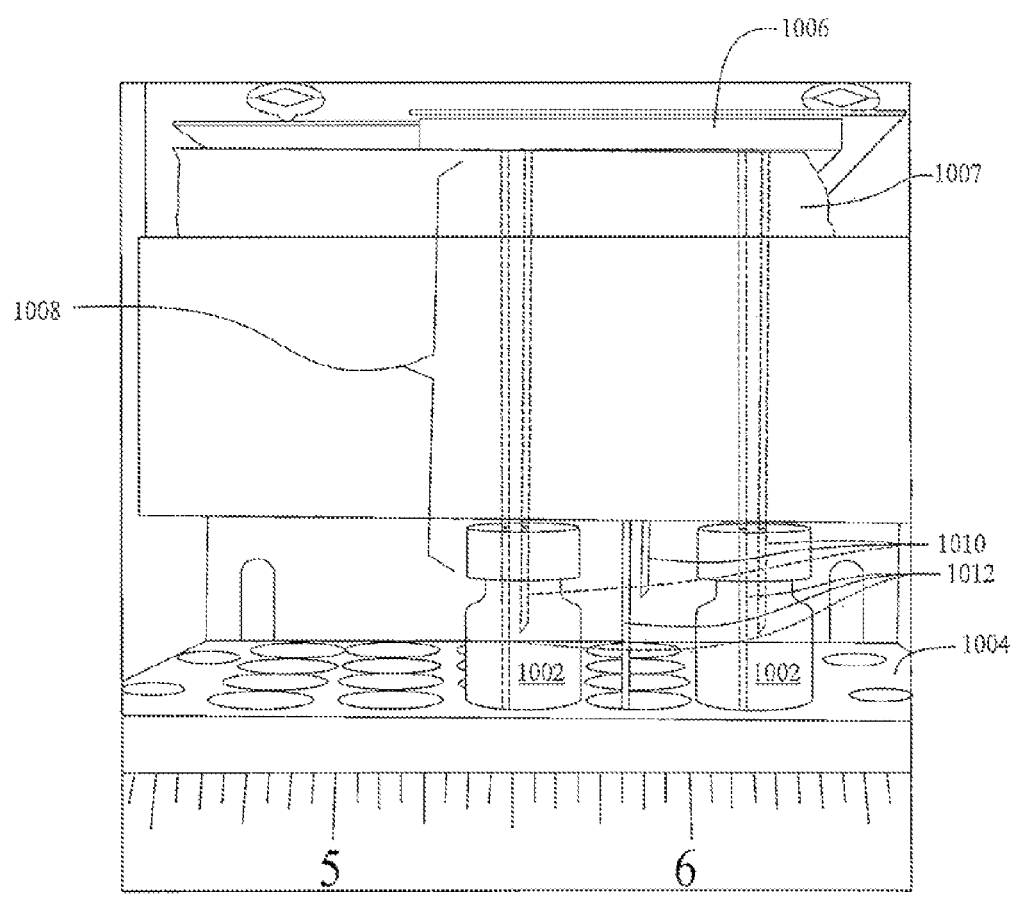
FIG. 10B depicts a front view of one embodiment of a multi-reagent loading setup for aqueous and non-aqueous reagents such as shown in FIG. 10A incorporating features of the present invention.

The present disclosure sets forth embodiments wherein a compact versatile multi-reagent loading system enables sequential on-demand loading during a multi-step chemical reaction. As shown in FIGS. 10A and 10B, sealed vials 1002 are arranged in a reagents cartridge 1004 and engaged to the EWOD chip 1006, which can be held in a gasket 1007, just before reaction via a fluidic interface 1008. Each vial is pierced by two needles comprising a longer liquid delivery needle 1010 going to the chip and a shorter gas delivery needle 1012 for introducing pressurised gas 1014 (for reagent vials) or vacuum (for product-vial and condensate-vial as discussed later) through software-controlled gas valves 1016 which can also direct the gas 1014 through a vent 1017. The needles can pierce the sealed vials at a capped septum 1018 allowing liquid to enter the loading site 1020. Pressure was applied to the vial until liquid was detected, for example via an electrode 1022, at the EWOD-actuated loading site on-chip. A droplet was then held by the EWOD, while gravity pulls back excess liquid to prevent flooding.

Figure 11:
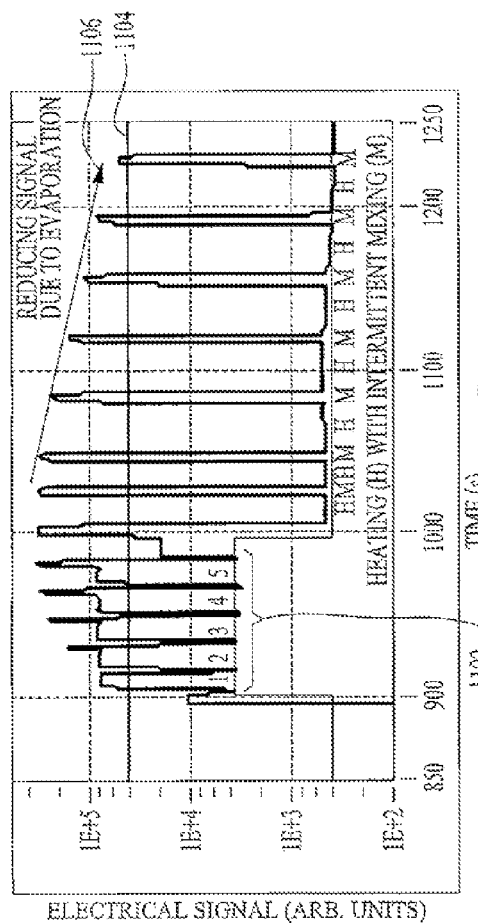
FIG. 11 is a graphical representation of impedance-based sensing detecting the presence of each loaded droplet according to the embodiment shown in FIGS. 10A-10B above.

FIG. 11 depicts a graphical representation of impedance-based, sensing detecting the presence of each loaded droplet according to the embodiment shown in FIGS. 10A-10B above, triggering the droplets transport to the reaction site by EWOD and enabling the droplet to continue to ensure automated delivery of the desired volume of each reagent to the reaction site. As shown in FIG. 11, the electrical signal is used for counting droplets (as represented by #1-5) 1102 of acetonitrile (MeCN) loaded onto the chip. As each droplet was loaded onto the chip, electrical impedance over the electrode changes, causing the signal to rise above the threshold 1104, and triggering droplet transport. Volume of liquid at the reaction site was monitored with an electrical signal, during resistive heating (H) interspersed with EWOD mixing (M) at software-controlled intervals. (Impedance signals were not available during heating steps). As the droplet evaporates during heating, the signal decrease 1106 corresponds to the lower volume.

Figures 12A, 12B, 12C, 12D, 12E:
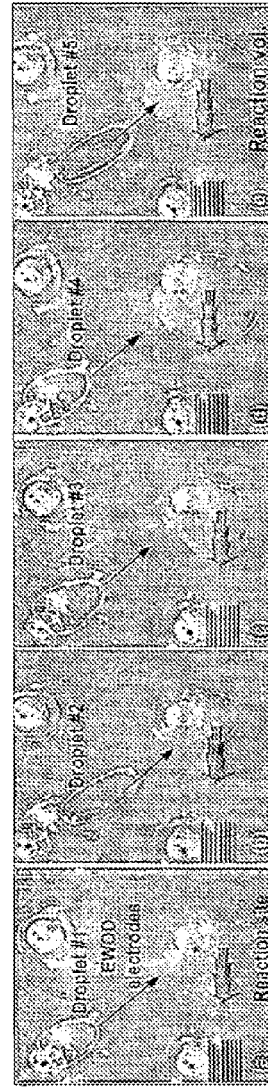

FIGS. 12A-12J displays an image sequence showing multiple droplet loading followed by heating with intermittent mixing, corresponding to FIG. 11. The reaction site was initially empty. FIGS. 12A-12E show the addition of droplets #1-#5 respectively loaded onto the chip from the inlet hole. FIGS. 12F-12H shows the droplets being transported by an EWOD to the reaction site. As shown in FIG. 12F, the heater electrodes are heated to e.g. 100° C. Condensation was then collected into a vial (not shown) using vacuum. Ring electrodes are intermittently software-toggled from heating to an EWOD for mixing. Concentric ring electrodes were used to perform evaporations or reactions at the desired (elevated) temperature once reagents have been loaded. By incorporating a software-controlled toggle between resistive temperature control and EWOD actuation, heating was interspersed with EWOD-driven mixing to maintain a homogeneous reaction mixture (FIGS. 12F-12J).

Automated extraction of products from the chip into a product vial was performed using software-controlled vacuum along with EWOD actuation. The overall system, comprising not only the chip but also off-chip components, is compact, automated, and amenable to the use of a disposable cartridge. Automation of all functionality is important not only to reduce human error but also to increase safety, especially for applications involving chemically hazardous reagents, and/or radioactive materials such as for the synthesis of positron, emission tomography (PET) probes.

FIGS. 13A-13H show a schematic representation (FIGS. 13A-13D) and a respective image sequence (FIGS. 13E-13H) showing multi-reagent loading and heating with mixing incorporating features of the present invention. As shown in FIG. 13A and FIG. 13E, reagent 1 droplet(s) 1302 are introduced from the corresponding inlet hole 1304 and transported by EWOD to the reaction site 1306. As discussed above, volumetric control of reagent introduced can be achieved by automated droplet counting. As shown in FIGS. 13B and 13F, resistive temperature control was used to set the appropriate temperature for the evaporation step 1320 or reaction step 1322; EWOD-driven mixing was intermittently performed during this step if needed. As discussed above, impedance based electrical sensing can be used to monitor the reaction volume. As shown in FIGS. 13C and 13G, reagent droplet(s) 1330 were added to the reaction site. As shown in FIGS. 13D and 13H, similar heating interspersed with EWOD mixing was performed, as per the desired reaction conditions. This process can be continued for additional reagents 1340 as required by the multi-step chemical synthesis.

FIGS. 14A and 14B shown schematic and image views of extraction electrodes 1402 incorporating features of the present invention. FIGS. 14A and 14B depict the extraction electrodes actuated to direct liquid 1404 towards an extraction hole 1406, while vacuum was applied to the product-vial to pull liquid off the chip.

Figures 15A, 15B:
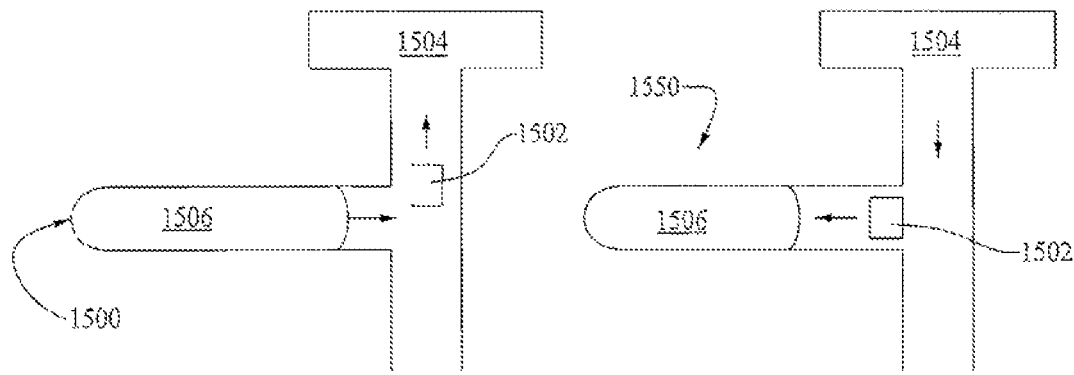
FIG. 15A is a schematic view of a thermopneumatic mechanism for delivery of reagents which incorporates features of the present invention.
FIG. 15B is a schematic view of a reversal of the thermopneumatic mechanism shown in FIG. 15A for retraction of reagents which incorporates features of the present invention.

Embodiments incorporating features of the present invention can use various other product and/or reagent delivery methods, for example, liquid actuation mechanisms independently or in combination with the gas-driven embodiments, with the disposability being maintained. For example, a thermopneumatic mechanism is set forth in FIGS. 15A and FIG. 15B. FIG. 15A is a schematic 1500 of such a thermopneumatic mechanism showing an example of an arrangement for driving a product or reagent 1502 to a chip 1504. Air 1506 (or other gas) is heated, causing the air 1506 to expand, which in turn pushes the reagent 1502 toward the chip 1504.

FIG. 15B is a schematic 1550, similar to schematic 1500 in FIG. 15A above, wherein like features are assigned like reference numbers, showing an example arrangement for pulling back excess product or reagent 1502 from the chip 1504. This pulling back or retraction is cause by cooling the air 1506 (or other gas) causing the air 1506 to contract, which in turn pulls the reagent 1502 away from the chip 1504 via a negative pressure differential. Methods utilized for heating and cooling the air 1506 can be any heating or cooling methods known in the art.

In some embodiments, thermoelectric (TEC) heating or cooling can be utilized. In these embodiments, utilizing TEC heating and/or cooling, a rapid response regarding the expansion or contraction of the air 1506 was elicited. A more passive heating or cooling system can be utilized in embodiments wherein a slower response is desired. Additionally, a combination of various heating and cooling systems can be utilizes, for example, both TEC and passive systems, such that both fast and slower responses can be elicited as desired.

Figure 16:
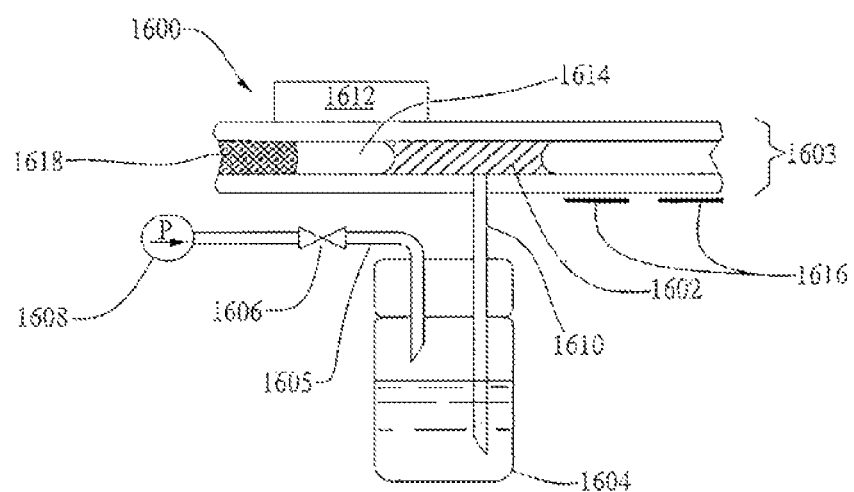
FIG. 16 is a schematic view of another thermopneumatic mechanism for delivery of reagents which incorporates features of the present invention.

FIG. 16 shows another example of an arrangement 1600 using a thermopneumatic mechanism for the delivery of reagent 1602, for example the delivery of a product or reagent 1602 to an EWOD chip 1603. A container 1604, such as a vial, was connected to a gas delivery needle 1605, which was connected to a valve 1606, which in turn was connected to a pump mechanism 1608. The valve, pump and gas delivery needle structure provides a mechanism for controlling, adjusting, and/or delivering the reagent 1602 within the container 1604, for example, as discussed in the various embodiments utilizing valves above.

Reagent 1602 travels through a liquid delivery needle 1610, wherein its travel is controlled by a heating and cooling system 1612, which acts upon air 1614 in a manner as disclosed above with regard to FIGS. 15A and 15B. The heating system can foe further controlled via electrodes 1616. A pressure sensitive adhesive (PSA) 1618 dam or a barrier of a thin sheet material can also be utilized to look in a quantity of air 1614 and to prevent the reagent 1602 from traveling in a given direction.

Figure 17:
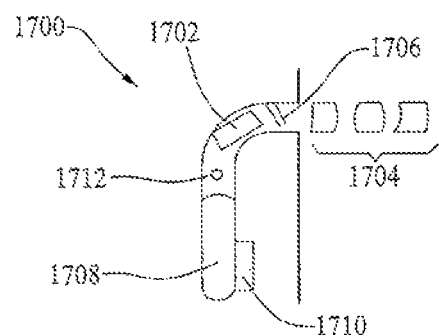
FIG. 17 is a schematic view of mechanism for delivery of reagents which incorporates a flexible barrier.

FIG. 17 shows another example of an arrangement 1700 of a mechanism for the delivery of liquid product or reagent 1702 which uses a bimetallic strip 1704 or a solenoid actuator to actuate a disposable flexible barrier or diaphragm 1706 in contact with the liquid, so as to create displacement of the liquid, for example, via surface tension. This arrangement 1700 can further comprise features of the above mentioned embodiments including trapped air 1708 which can be heated or cooled by a TEC heater 1710. The liquid reagent 1702 can be introduced into the arrangement 1700 via an entry point 1712.

Figure 18A:
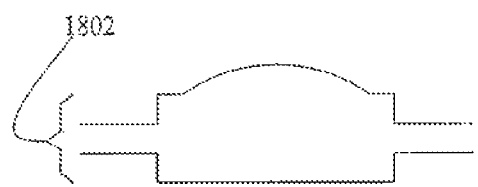
FIGS. 18A-18B show a schematic view of mechanism using a valve mechanism for delivery of reagents which incorporates features of the present invention.
Figure 18B:
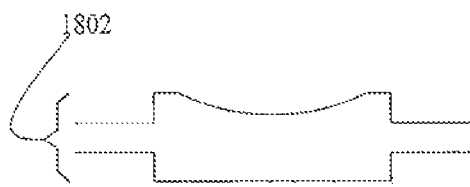

As shown in FIGS. 18A and 18B, a pullback actuator can also be utilized to displace product or reagent, for example by creating a valve-like structure 1802. FIG. 18A shows the actuator in an actuated open position in which reagent can freely pass through the valve structure. FIG. 18B shows the actuator in an unactuated closed position in which reagent flow through valve structure is restricted. In some embodiments, the actuation of the pull back actuator itself can cause fluid to be moved in a direction toward the pull back actuator.

Figure 19:
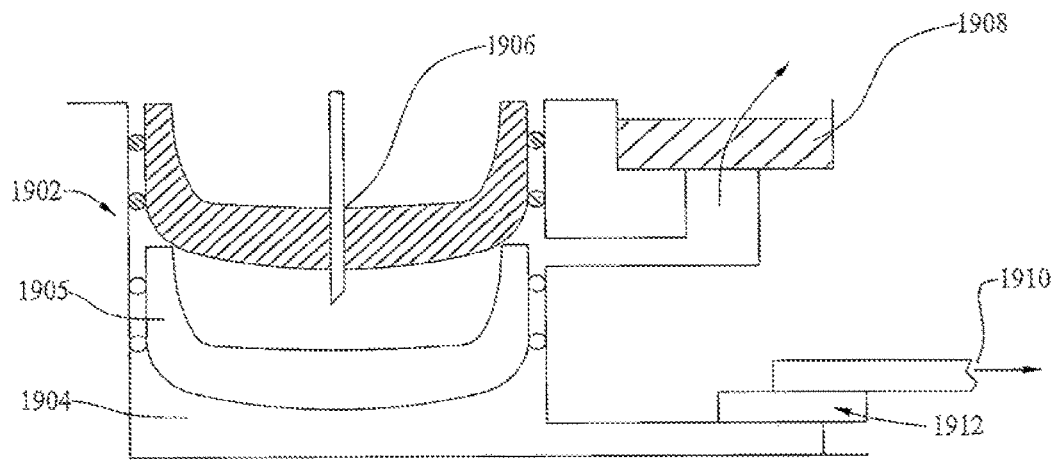
FIG. 19 shows a schematic view of a plunger mechanism, for delivery of reagents which incorporates features of the present invention.

FIG. 19 shows a further embodiment of a mechanism 1902 for the delivery of product or reagent. The image shows a reservoir 1904 molded into a disposable unit that mates with the chip 1902. By actuation of a plunger 1905, these reservoirs 1904 can deliver reagents to a chip, or collect liquids from a chip. The reservoirs can be filled or content such as reagent product and/or air removed by utilizing a syringe 1906, which can, for example pierce a septum of the mechanism as in the embodiments discussed above. As shown in FIG. 19, actuation and de-actuation of the plunger can adjust the internal pressure and displacement, of mechanism 1902 through venting air via a filter vent 1908, such as a Polytetrafluoroethylene (PTFE) filter vent, can distribute liquid reagent to the chip at point 1910. The mechanism 1902 can further comprise a capillary not shown) and a capillary stop 1912 that can be adjusted to stop capillary flow during filling of the mechanism 1902.

Figure 20:
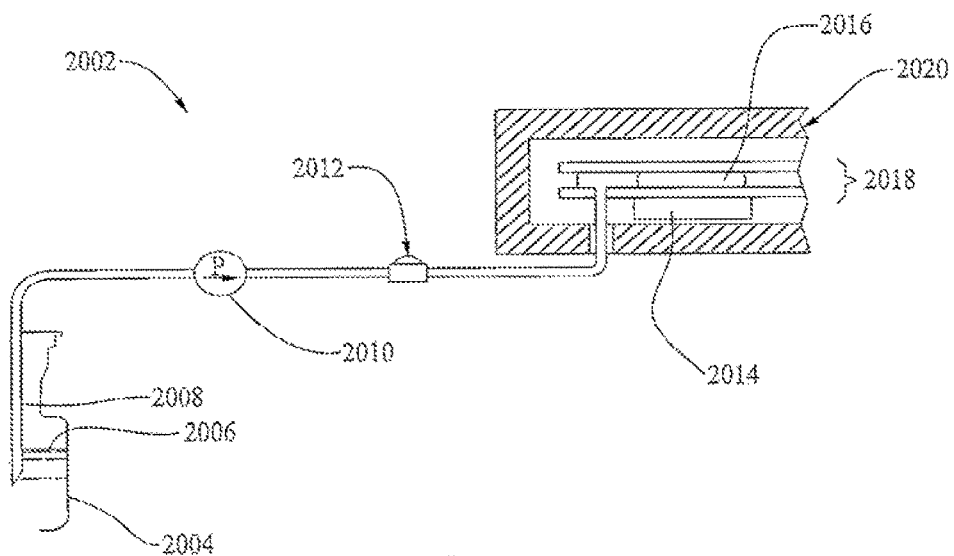
FIG. 20 shows a schematic view of an assembly using a combination of mechanisms for delivery of reagents which incorporates features of the present invention.

One or more of the above disclosed delivery mechanisms could be combined either with a gas-driven liquid pumping mechanism, or other pumping mechanisms such as positive displacement (e.g. peristaltic) pump which use only disposable wetted components FIG. 20. The fluid paths including deformable tubing can also be made by a combination of various processes, such as molding and laminating fabrication techniques. An example of such a combination arrangement 2002 is depicted in FIG. 20. FIG. 20 shows a container 2004 containing a reagent 2006. A liquid delivery needle 2008 with an end immersed in the reagent 2006 is arranged in communication with, a positive displacement pump 2010, for example a peristaltic pump. Downstream from the positive displacement pump 2010 is a pullback actuator 2012 and downstream of the pull back actuator 2012 is an arrangement comprising a TEC 2014, which can interact with trapped air 2016 to further deliver liquid to and from an EWOD chip 2018. This arrangement can further comprise a lead shield 2020 for protection against radioactive elements Interfacing the exit end of the chip can lead to a variety of downstream elements such as another chip, vial or device (for further processing or reactions), purification systems such as a cartridge purification system, a preparative high-performance liquid chromatography (HPLC) system capillary electrophoresis system, etc., analytical systems such as HPLC, gas chromatography (GC), spectroscopy system, etc., reformulation systems such as rotary evaporator (rotovap), microscale or macroscale solvent exchange systems, etc., and/or direct delivery into an animal or human. Additionally, liquid from the chip can be divided into multiple pathways leading to more than one of the above downstream, elements.

The area on the chip around each inlet or outlet can be open, or provided with additional physical structures in order to better guide the liquid into and out of the chip. For example, there can be structure (made from adhesive or non-adhesive material or a combination thereof, for example made from the same material used as a spacer between two EWOD chip substrates), to prevent liquid from moving away from the electrodes as illustrate below. This would help to minimize the structure needed for each inlet and outlet pathway while avoiding cross-contamination.

Figure 21:
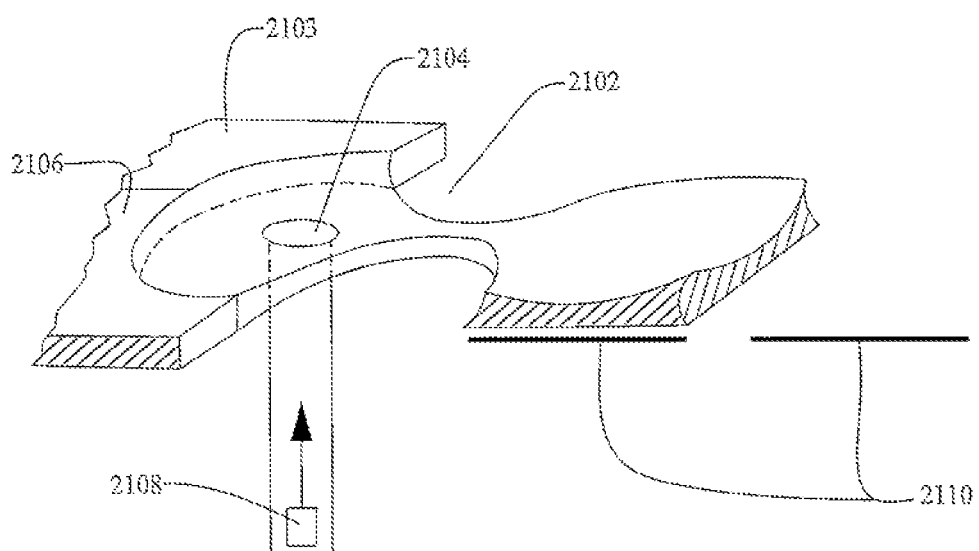
FIG. 21 shows a schematic view of mechanism for delivery of reagents that incorporate features of the present invention.

Similarly, as depicted in FIG. 21 the region 2102 surrounding the interface out of the chip 2103 could be open to air, or modified in order to guide the liquid towards the chip outlet 2104. The outlet can be at least partially bound by physical structure(s) and/or surface modification, such as a PSA or film dam 2106 in order to better direct the flow of reagent 2108 towards the outlet hole 2104. Reagent flow can further be controlled via a TEC system setup utilizing electrodes 2110.

There are numerous ways that an on-chip sample can be moved to the extraction/collection point on the chip. For example, actuation of EWOD electrodes can be used to move (or change the shape of the sample droplet) such that a portion of it is situated covering the hole in the EWOD chip. Vacuum can then be applied to the collection fluid path to draw the sample into the fluid path towards the sample destination. Another mechanism that can be used is to apply vacuum at the collection fluid path which will create a flow pattern in the gas that fills the space between the substrates of the chip that can move (or change the shape of the sample droplet) to situate it over the hole in the chip. Physical structures surrounding the outlet hole can help create the desired flow pattern.

Collection can also be accomplished by other mechanisms. For example, a very fine capillary, fibrous thread or "paper", or porous media (packed beads or porous polymer monolith) could foe placed adjacent ho the reaction site, such that the droplet can be brought into contact with this structure, and then pulled out of the chip by capillary forces for delivery to another location. Besides the gas-based selector valves described in one embodiment above, and as appropriate for the application, the interface can include disposable liquid valves such as stopcock valves no allow selection between different inlets and outlets.

Although the present invention has been described in detail with reference to certain preferred configurations thereof, other versions are possible. Embodiments of the present invention can comprise any combination of compatible features shown in the various figures, and these embodiments should not be limited to those expressly illustrated and discussed. Therefore, the spirit and scope of the invention should not be limited to the versions described above.

We claim:

1. A digital microfluidic chip interface assembly comprising:
   a microfluidic chip comprising a first planar substrate and a second planar substrate separated from the first planar substrate by a gap extending along a length of the first planar substrate and the second planar substrate, wherein at least one of the first planar substrate and the second planar substrate comprises EWOD electrodes disposed thereon;
   at least one liquid containing reagent container positioned so that a droplet of the liquid therein can be delivered to the gap of the microfluidic chip through a fluid pathway between each of the at least one reagent containers to the microfluidic chip;
   a regulated gas pressure source in communication with the at least one liquid reagent container via a valve, wherein actuation of the valve transfers liquid from the at least one liquid reagent container to the gap of the microfluidic chip to form the droplet;
   at least one product container positioned for receiving a product in a liquid carrier droplet from the gap in the microfluidic chip through a fluid pathway between the microfluidic chip and the at least one product container; and a regulated vacuum source in communication with the at least one product container via a valve, wherein actuation of the valve transfers the droplet from the gap to the at least one product container.

2. The interface assembly of claim 1, wherein the regulated gas pressure source comprises one of a positive pressure pump, a positive displacement pump, and pullback actuator.

3. The interface assembly of claim 1, wherein the regulated vacuum source is connected to multiple product containers through a selector valve.

4. The interface assembly of claim 1, wherein fluid pathway between the microfluidic chip and the at least one product container further comprises a purification cartridge.

5. The interface assembly of claim 4, further comprising one or more receptacles disposed in the fluid pathway between the microfluidic chip and the at least one product container, wherein the one or more receptacles comprise at least one waste receptacle to receive filtered waste from the purification cartridge.

6. The interface assembly of claim 5, wherein the one or more receptacles comprise at least one product receptacle to receive purified product.

7. The interface assembly of claim 5, wherein the one or more receptacles comprise at least one degassing vial that receives gas removed from the product.

8. The interface assembly of claim 3, wherein the interface assembly comprises a computer configured to operate the selector valve.

9. The interface assembly of claim 1, wherein the interface further comprises an electrical impedance sensor configured to count droplets of reagent delivered to the gap of the microfluidic chip.

10. The interface assembly of claim 4, wherein the purification cartridge is configured to remove impurities, or to trap the product on the cartridge.

11. The interface assembly of claim 10, further comprising an elutent source switchable into the fluid path containing the purification cartridge.

12. The interface assembly of claim 11, further comprising an external system comprising an HPLC or analytical instrument.

13. A digital microfluidic chip interface assembly comprising:
a microfluidic chip comprising a first planar substrate and a second planar substrate separated from the first planar substrate by a gap extending along a length of the first planar substrate and the second planar substrate, wherein the first planar substrate comprises EWOD electrodes disposed thereon and includes an inlet hole and an extraction hole;
a sealed reagent container containing liquid reagent therein;
a first fluid pathway extending into the sealed reagent container and connecting to the inlet hole;
a second fluid pathway extending into the sealed reagent container and connected to a gas pressure source via a first valve, wherein actuation of the first valve transfers liquid reagent from the sealed reagent container to the gap of the microfluidic chip via the first fluid pathway to form a droplet;
a sealed product container coupled to the extraction hole;
a third fluid pathway extending from the extraction hole and into the sealed product container;
a fourth fluid pathway extending into the sealed product container and connected to a vacuum source via a second valve, wherein actuation of the second valve transfers a droplet from the gap to the sealed product container.

14. The interface assembly of claim 13, further comprising a purification cartridge disposed in the fourth fluid pathway.

15. A digital microfluidic chip interface assembly comprising:
a microfluidic chip comprising a first planar substrate and a second planar substrate separated from the first planar substrate by a gap extending along a length of the first planar substrate and the second planar substrate, wherein at least one of the first planar substrate and the second planar substrate comprises EWOD electrodes disposed thereon;
at least one liquid containing reagent container positioned so that a droplet of the liquid therein can be delivered to the gap of the microfluidic chip through a fluid pathway between each of the at least one reagent containers to the microfluidic chip;
a first positive displacement pump in communication with the at least one liquid reagent container, wherein actuation of the first positive displacement pump transfers liquid from the at least one liquid reagent container to the gap of the microfluidic chip to form the droplet;
at least one product container positioned for receiving a product in a liquid carrier droplet from the gap in the microfluidic chip through a fluid pathway between the microfluidic chip and the at least one product container; and
a second positive displacement pump in communication with the at least one product container, wherein actuation of the second positive displacement pump transfers the droplet from the gap to the at least one product container.

16. The interface assembly of claim 15, wherein the first positive displacement pump and the second positive displacement pump comprise peristaltic pumps.

* * * * *